US012582822B2

(12) United States Patent
Papay et al.

(10) Patent No.: US 12,582,822 B2
(45) Date of Patent: Mar. 24, 2026

(54) INTRA-ORAL APPLIANCES AND SYSTEMS

(71) Applicants: THE CLEVELAND CLINIC FOUNDATION, Cleveland, OH (US); XII Medical, Inc., Cleveland, OH (US)

(72) Inventors: Francis A. Papay, Westlake, OH (US); Kelly B. Emerton, Bay Village, OH (US); Charles P. Steiner, Pepper Pike, OH (US); Anthony V. Caparso, North Ridgeville, OH (US)

(73) Assignees: The Cleveland Clinic Foundation, Cleveland, OH (US); XII Medical, Inc., Union City, CA (US)

( * ) Notice: Subject to any disclaimer, the term of this patent is extended or adjusted under 35 U.S.C. 154(b) by 113 days.

(21) Appl. No.: 17/804,731

(22) Filed: May 31, 2022

(65) Prior Publication Data

US 2022/0288390 A1     Sep. 15, 2022

Related U.S. Application Data

(63) Continuation of application No. 16/865,363, filed on May 3, 2020, now Pat. No. 11,351,377.

(Continued)

(51) Int. Cl.
  *A61N 1/36*        (2006.01)
  *A61N 1/05*        (2006.01)
  (Continued)

(52) U.S. Cl.
  CPC .......... *A61N 1/3611* (2013.01); *A61N 1/0548* (2013.01); *A61N 1/36078* (2013.01);
  (Continued)

(58) Field of Classification Search
  CPC ........................... A61N 1/0548; A61N 1/3611; A61N 1/36078; A61N 1/36128; A61N 1/37205;
  (Continued)

(56) References Cited

U.S. PATENT DOCUMENTS

| | | | |
|---|---|---|---|
| 910,774 A | 1/1909 | Beers | |
| 4,990,160 A | 2/1991 | Terino | |

(Continued)

FOREIGN PATENT DOCUMENTS

| | | |
|---|---|---|
| EP | 3962593 B1 | 7/2023 |
| EP | 4241690 A2 | 9/2023 |

(Continued)

OTHER PUBLICATIONS

Decker, Michael J., et al. "Functional electrical stimulation and respiration during sleep." Journal of Applied Physiology 75.3 (1993): 1053-1061.

(Continued)

*Primary Examiner* — Unsu Jung
*Assistant Examiner* — Laura Hodge
(74) *Attorney, Agent, or Firm* — Fortem IP LLP

(57) ABSTRACT
An intra-oral appliance to power and/or communicate with a neurostimulator is provided. The intra-oral appliance can include a teeth covering configured to fit over mandibular incisor, canine and/or premolar teeth of a human being and a remote controller in the form of a housing extending posteriorly from and operably connected to the teeth covering. The housing can include a power source, a coupling coil configured to transmit power to the neurostimulator and configured to receive power from an external charger, and electrical circuitry operably connected to the coupling coil and the power source.

21 Claims, 4 Drawing Sheets

*10*

*52*

Related U.S. Application Data

(60) Provisional application No. 62/842,890, filed on May 3, 2019.

(51) Int. Cl.
　*A61N 1/372* (2006.01)
　*A61N 1/40* (2006.01)

(52) U.S. Cl.
　CPC ..... *A61N 1/36128* (2013.01); *A61N 1/37252* (2013.01); *A61N 1/40* (2013.01)

(58) Field of Classification Search
　CPC .............. A61N 1/37252; A61N 1/3756; A61N 1/3787; A61N 1/40
　USPC ........................................................ 607/19
　See application file for complete search history.

(56) References Cited

U.S. PATENT DOCUMENTS

| | | | |
|---|---|---|---|
| 5,335,657 | A | 8/1994 | Terry et al. |
| 5,522,862 | A | 6/1996 | Testerman et al. |
| 5,591,216 | A | 1/1997 | Testerman et al. |
| 5,609,621 | A | 3/1997 | Bonner |
| 5,716,377 | A | 2/1998 | Rise et al. |
| 5,877,466 | A | 3/1999 | Bolongeat-Mobleu et al. |
| 5,988,171 | A | 11/1999 | Sohn et al. |
| 6,240,316 | B1 | 5/2001 | Richmond et al. |
| 6,314,324 | B1 | 11/2001 | Lattner et al. |
| 6,345,202 | B2 | 2/2002 | Richmond et al. |
| 6,587,725 | B1 | 7/2003 | Durand et al. |
| 6,770,022 | B2 | 8/2004 | Mechlenburg et al. |
| 7,660,632 | B2 | 2/2010 | Kirby et al. |
| 7,668,591 | B2 | 2/2010 | Lee et al. |
| 7,680,538 | B2 | 3/2010 | Durand et al. |
| 7,711,438 | B2 | 5/2010 | Lattner et al. |
| 7,885,713 | B2 | 2/2011 | Campbell et al. |
| 8,204,602 | B2 | 6/2012 | Kallmyer |
| 8,255,056 | B2 | 8/2012 | Tehrani |
| 8,498,712 | B2 | 7/2013 | Bolea et al. |
| 8,498,713 | B2 | 7/2013 | Mcclure et al. |
| 8,574,164 | B2 | 11/2013 | Mashiach |
| 8,577,464 | B2 | 11/2013 | Mashiach |
| 8,577,465 | B2 | 11/2013 | Mashiach |
| 8,577,466 | B2 | 11/2013 | Mashiach |
| 8,577,467 | B2 | 11/2013 | Mashiach et al. |
| 8,577,468 | B2 | 11/2013 | Mashiach et al. |
| 8,577,472 | B2 | 11/2013 | Mashiach et al. |
| 8,577,478 | B2 | 11/2013 | Mashiach et al. |
| 8,577,647 | B2 | 11/2013 | Farritor et al. |
| 8,585,617 | B2 | 11/2013 | Mashiach et al. |
| 8,588,941 | B2 | 11/2013 | Mashiach |
| 8,626,304 | B2 | 1/2014 | Bolea et al. |
| 8,644,957 | B2 | 2/2014 | Mashiach |
| 8,700,183 | B2 | 4/2014 | Mashiach |
| 8,718,776 | B2 | 5/2014 | Mashiach et al. |
| 8,744,589 | B2 | 6/2014 | Bolea et al. |
| 8,751,005 | B2 | 6/2014 | Meadows et al. |
| 8,798,773 | B2 | 8/2014 | Mashiach |
| 8,812,113 | B2 | 8/2014 | Mashiach |
| 8,812,135 | B2 | 8/2014 | Mashiach |
| 8,831,730 | B2 | 9/2014 | Mashiach et al. |
| 8,838,256 | B2 | 9/2014 | Mashiach et al. |
| 8,897,880 | B2 | 11/2014 | Mashiach |
| 8,897,895 | B2 | 11/2014 | Mashiach |
| 8,903,493 | B2 | 12/2014 | Mashiach et al. |
| 8,903,515 | B2 | 12/2014 | Mashiach |
| 8,948,871 | B2 | 2/2015 | Mashiach et al. |
| 8,958,893 | B2 | 2/2015 | Mashiach |
| 8,989,868 | B2 | 3/2015 | Mashiach et al. |
| 9,031,653 | B2 | 5/2015 | Mashiach |
| 9,031,654 | B2 | 5/2015 | Meadows et al. |
| 9,044,612 | B2 | 6/2015 | Mashiach et al. |
| 9,061,151 | B2 | 6/2015 | Mashiach et al. |
| 9,061,162 | B2 | 6/2015 | Mashiach et al. |
| 9,095,725 | B2 | 8/2015 | Mashiach |
| 9,101,774 | B2 | 8/2015 | Mashiach et al. |
| 9,155,899 | B2 | 10/2015 | Mashiach et al. |
| 9,186,511 | B2 | 11/2015 | Bolea |
| 9,220,907 | B2 | 12/2015 | Maschiach et al. |
| 9,220,908 | B2 | 12/2015 | Mashiach |
| 9,248,290 | B2 | 2/2016 | Mashiach |
| 9,248,291 | B2 | 2/2016 | Mashiach |
| 9,248,302 | B2 | 2/2016 | Mashiach et al. |
| 9,259,585 | B2 | 2/2016 | Vajha et al. |
| 9,302,093 | B2 | 4/2016 | Mashiach |
| 9,308,370 | B2 | 4/2016 | Lima et al. |
| 9,308,381 | B2 | 4/2016 | Mashiach et al. |
| 9,314,613 | B2 | 4/2016 | Mashiach |
| 9,314,641 | B2 | 4/2016 | Meadows et al. |
| 9,327,132 | B2 | 5/2016 | Mashiach |
| 9,339,651 | B2 | 5/2016 | Meadows et al. |
| 9,358,392 | B2 | 6/2016 | Mashiach |
| 9,370,657 | B2 | 6/2016 | Tehrani et al. |
| 9,393,435 | B2 | 7/2016 | Mashiach |
| 9,403,009 | B2 | 8/2016 | Mashiach |
| 9,403,025 | B2 | 8/2016 | Mashiach et al. |
| 9,409,013 | B2 | 8/2016 | Mashiach et al. |
| 9,415,215 | B2 | 8/2016 | Mashiach |
| 9,415,216 | B2 | 8/2016 | Mashiach |
| 9,421,372 | B2 | 8/2016 | Mashiach et al. |
| 9,463,318 | B2 | 10/2016 | Mashiach et al. |
| 9,486,628 | B2 | 11/2016 | Christopherson et al. |
| 9,757,560 | B2 | 9/2017 | Papay |
| 9,849,288 | B2 | 12/2017 | Meadows et al. |
| 9,950,166 | B2 | 4/2018 | Mashiach et al. |
| 10,029,098 | B2 | 7/2018 | Papay |
| 10,065,038 | B2 | 9/2018 | Papay |
| 10,105,538 | B2 | 10/2018 | Bolea et al. |
| 10,238,468 | B2 | 3/2019 | Forsell |
| 10,675,467 | B2 | 6/2020 | Papay |
| 11,291,842 | B2 | 4/2022 | Caparso et al. |
| 11,338,142 | B2 | 5/2022 | Papay |
| 11,351,377 | B2 | 6/2022 | Papay et al. |
| 11,351,380 | B2 | 6/2022 | Caparso et al. |
| 11,420,061 | B2 | 8/2022 | Caparso et al. |
| 11,420,063 | B2 | 8/2022 | Caparso et al. |
| 11,491,333 | B2 | 11/2022 | Papay |
| 11,691,010 | B2 | 7/2023 | Caparso et al. |
| 11,712,565 | B2 | 8/2023 | Papay |
| 11,771,899 | B2 | 10/2023 | Papay et al. |
| 11,869,211 | B2 | 1/2024 | Caparso et al. |
| 11,883,667 | B2 | 1/2024 | Caparso et al. |
| 12,172,013 | B2 | 12/2024 | Caparso et al. |
| 12,434,058 | B2 | 10/2025 | Papay |
| 2002/0010495 | A1 | 1/2002 | Tucker et al. |
| 2005/0076908 | A1 | 4/2005 | Lee et al. |
| 2006/0122662 | A1 | 6/2006 | Tehrani et al. |
| 2006/0224211 | A1 | 10/2006 | Durand et al. |
| 2007/0160274 | A1 | 7/2007 | Mashiach |
| 2007/0239230 | A1 | 10/2007 | Giftakis et al. |
| 2007/0263915 | A1 | 11/2007 | Mashiach |
| 2008/0039904 | A1 | 2/2008 | Beutler et al. |
| 2008/0082147 | A1 | 4/2008 | Dai et al. |
| 2008/0260217 | A1 | 10/2008 | Mashiach |
| 2008/0260229 | A1 | 10/2008 | Mashiach |
| 2009/0082831 | A1 | 3/2009 | Paul et al. |
| 2009/0226057 | A1 | 9/2009 | Mashiach et al. |
| 2009/0270960 | A1 | 10/2009 | Zhao et al. |
| 2010/0016749 | A1 | 1/2010 | Atsma et al. |
| 2010/0094379 | A1 | 4/2010 | Meadows et al. |
| 2010/0174341 | A1* | 7/2010 | Bolea ................... A61B 5/4818 607/42 |
| 2010/0179562 | A1 | 7/2010 | Linker et al. |
| 2010/0241195 | A1 | 9/2010 | Meadows et al. |
| 2010/0260217 | A1 | 10/2010 | Redford |
| 2010/0280568 | A1 | 11/2010 | Bulkes et al. |
| 2010/0292769 | A1 | 11/2010 | Brounstein et al. |
| 2011/0071606 | A1 | 3/2011 | Kast et al. |
| 2011/0093032 | A1 | 4/2011 | Boggs et al. |
| 2011/0093036 | A1 | 4/2011 | Mashiach |
| 2011/0125212 | A1 | 5/2011 | Tyler |
| 2011/0137376 | A1 | 6/2011 | Meskens |
| 2011/0230702 | A1 | 9/2011 | Honour |

(56)        References Cited

U.S. PATENT DOCUMENTS

| | | |
|---|---|---|
| 2012/0010532 A1 | 1/2012 | Bolea et al. |
| 2012/0010681 A1 | 1/2012 | Bolea et al. |
| 2013/0085537 A1 | 4/2013 | Mashiach |
| 2013/0085558 A1 | 4/2013 | Mashiach |
| 2013/0204097 A1 | 8/2013 | Rondoni et al. |
| 2013/0289401 A1 | 10/2013 | Colbaugh et al. |
| 2014/0031840 A1 | 1/2014 | Mashiach |
| 2014/0031902 A1 | 1/2014 | Mashiach et al. |
| 2014/0031903 A1 | 1/2014 | Mashiach |
| 2014/0031904 A1 | 1/2014 | Mashiach |
| 2014/0046221 A1 | 2/2014 | Mashiach et al. |
| 2014/0052219 A1 | 2/2014 | Mashiach et al. |
| 2014/0100642 A1 | 4/2014 | Mashiach |
| 2014/0135868 A1 | 5/2014 | Bashyam |
| 2014/0172061 A1 | 6/2014 | Mashiach |
| 2014/0228905 A1* | 8/2014 | Bolea ...................... A61F 5/566 |
| | | 607/42 |
| 2014/0266933 A1 | 9/2014 | Andersen et al. |
| 2014/0358026 A1 | 12/2014 | Mashiach et al. |
| 2014/0358189 A1 | 12/2014 | Mashiach et al. |
| 2014/0358196 A1 | 12/2014 | Mashiach |
| 2014/0358197 A1 | 12/2014 | Mashiach et al. |
| 2014/0371802 A1 | 12/2014 | Mashiach et al. |
| 2014/0371817 A1 | 12/2014 | Mashiach et al. |
| 2014/0379049 A1 | 12/2014 | Mashiach et al. |
| 2015/0032177 A1 | 1/2015 | Mashiach et al. |
| 2015/0073232 A1 | 3/2015 | Ahmad et al. |
| 2015/0077308 A1 | 3/2015 | Jeon et al. |
| 2015/0088025 A1 | 3/2015 | Litvak et al. |
| 2015/0096167 A1 | 4/2015 | Zhao et al. |
| 2015/0112402 A1 | 4/2015 | Mashiach |
| 2015/0112416 A1 | 4/2015 | Mashiach et al. |
| 2015/0142120 A1 | 5/2015 | Papay |
| 2015/0196766 A1 | 7/2015 | Rosenberg et al. |
| 2015/0224307 A1 | 8/2015 | Bolea |
| 2015/0265221 A1 | 9/2015 | Flanagan et al. |
| 2015/0283313 A1 | 10/2015 | Huber |
| 2015/0290454 A1 | 10/2015 | Eugene et al. |
| 2015/0290465 A1 | 10/2015 | Mashiach |
| 2015/0343221 A1 | 12/2015 | Mashiach |
| 2016/0094082 A1 | 3/2016 | Ookawa et al. |
| 2016/0106976 A1 | 4/2016 | Kucklick |
| 2016/0121121 A1 | 5/2016 | Mashiach |
| 2016/0121122 A1 | 5/2016 | Mashiach |
| 2016/0166828 A1* | 6/2016 | Yu ......................... A61N 1/0553 |
| | | 607/116 |
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0287863 A1* | 10/2016 | Mercanzini .............. A61B 5/24 |
| 2016/0346537 A1 | 12/2016 | Mashiach |
| 2017/0087360 A1* | 3/2017 | Scheiner ............ A61N 1/37229 |
| 2017/0106190 A1 | 4/2017 | Papay |
| 2017/0143257 A1 | 5/2017 | Kent et al. |
| 2017/0143280 A1 | 5/2017 | Kent |
| 2017/0274210 A1 | 9/2017 | Papay |
| 2017/0290699 A1 | 10/2017 | Radmand |
| 2017/0296815 A1 | 10/2017 | Papay |
| 2018/0015282 A1* | 1/2018 | Waner ...................... A61B 5/00 |
| 2018/0028824 A1 | 2/2018 | Pivonka et al. |
| 2018/0117313 A1 | 5/2018 | Schmidt et al. |
| 2018/0191069 A1 | 7/2018 | Chen et al. |
| 2018/0200512 A1 | 7/2018 | Bolea et al. |
| 2018/0221673 A1 | 8/2018 | Kuang |
| 2018/0280694 A1 | 10/2018 | Mashiach et al. |
| 2019/0117966 A1 | 4/2019 | Kent |
| 2019/0151656 A1 | 5/2019 | Bolea et al. |
| 2019/0160282 A1 | 5/2019 | Dieken et al. |
| 2019/0247664 A1 | 8/2019 | Irazoqui et al. |
| 2020/0016401 A1 | 1/2020 | Papay et al. |
| 2020/0269044 A1 | 8/2020 | Papay |
| 2020/0338358 A1* | 10/2020 | Makansi ............ A61N 1/36125 |
| 2020/0346010 A1 | 11/2020 | Papay et al. |
| 2020/0346016 A1 | 11/2020 | Caparso et al. |
| 2020/0346017 A1 | 11/2020 | Caparso et al. |
| 2020/0346024 A1 | 11/2020 | Caparso et al. |
| 2021/0106824 A1 | 4/2021 | Caparso et al. |
| 2021/0128914 A1 | 5/2021 | Papay |
| 2022/0218988 A1 | 7/2022 | Caparso et al. |
| 2022/0241588 A1 | 8/2022 | Caparso et al. |
| 2022/0266030 A1 | 8/2022 | Caparso et al. |
| 2022/0323752 A1 | 10/2022 | Papay |
| 2022/0370798 A1 | 11/2022 | Caparso et al. |
| 2022/0401738 A1 | 12/2022 | Caparso et al. |
| 2023/0024498 A1 | 1/2023 | Caparso et al. |
| 2023/0277843 A1 | 9/2023 | Caparso et al. |
| 2023/0310860 A1 | 10/2023 | Papay |
| 2024/0066300 A1 | 2/2024 | Papay et al. |
| 2024/0198108 A1 | 6/2024 | Caparso et al. |
| 2025/0065119 A1 | 2/2025 | Caparso et al. |
| 2025/0195893 A1 | 6/2025 | Caparso et al. |

FOREIGN PATENT DOCUMENTS

| | | |
|---|---|---|
| EP | 3962585 B1 | 5/2024 |
| EP | 4431008 A2 | 9/2024 |
| JP | 2013208182 A | 10/2013 |
| JP | 2013543741 A | 12/2013 |
| JP | 2019503722 A | 2/2019 |
| WO | 9219318 A1 | 11/1992 |
| WO | 2005018737 A1 | 3/2005 |
| WO | 2007080579 A2 | 7/2007 |
| WO | 2007080579 A3 | 7/2007 |
| WO | 2007080580 A2 | 7/2007 |
| WO | 2007080580 A3 | 7/2007 |
| WO | 2008129545 A1 | 10/2008 |
| WO | 2009007896 A2 | 1/2009 |
| WO | 2009007896 A3 | 1/2009 |
| WO | 2009109971 A2 | 9/2009 |
| WO | 2009109971 A3 | 9/2009 |
| WO | 2009143560 A1 | 12/2009 |
| WO | 2010006218 A2 | 1/2010 |
| WO | 2011048590 A1 | 4/2011 |
| WO | 2011077433 A1 | 6/2011 |
| WO | 2013046032 A2 | 4/2013 |
| WO | 2013046032 A3 | 4/2013 |
| WO | 2013046035 A2 | 4/2013 |
| WO | 2013046035 A3 | 4/2013 |
| WO | 2013046038 A2 | 4/2013 |
| WO | 2013046038 A3 | 4/2013 |
| WO | 2013046039 A2 | 4/2013 |
| WO | 2013046039 A3 | 4/2013 |
| WO | 2013046040 A2 | 4/2013 |
| WO | 2013046040 A3 | 4/2013 |
| WO | 2013046042 A2 | 4/2013 |
| WO | 2013046042 A3 | 4/2013 |
| WO | 2013046043 A2 | 4/2013 |
| WO | 2013046043 A3 | 4/2013 |
| WO | 2013046044 A2 | 4/2013 |
| WO | 2013046044 A3 | 4/2013 |
| WO | 2013046048 A2 | 4/2013 |
| WO | 2013046048 A3 | 4/2013 |
| WO | 2013046049 A2 | 4/2013 |
| WO | 2013046049 A3 | 4/2013 |
| WO | 2013046053 A2 | 4/2013 |
| WO | 2013046053 A3 | 4/2013 |
| WO | 2013057594 A2 | 4/2013 |
| WO | 2013057594 A3 | 4/2013 |
| WO | 2013057597 A1 | 4/2013 |
| WO | 2013061164 A2 | 5/2013 |
| WO | 2013061164 A3 | 5/2013 |
| WO | 2013061169 A2 | 5/2013 |
| WO | 2013061169 A3 | 5/2013 |
| WO | 2013177621 A1 | 12/2013 |
| WO | 2014016684 A2 | 1/2014 |
| WO | 2014016684 A3 | 1/2014 |
| WO | 2014016686 A2 | 1/2014 |
| WO | 2014016686 A3 | 1/2014 |
| WO | 2014016687 A2 | 1/2014 |
| WO | 2014016687 A3 | 1/2014 |
| WO | 2014016688 A2 | 1/2014 |
| WO | 2014016688 A3 | 1/2014 |
| WO | 2014016691 A2 | 1/2014 |
| WO | 2014016691 A3 | 1/2014 |

(56)          References Cited

FOREIGN PATENT DOCUMENTS

| WO | 2014016692 A2 | 1/2014 |
| WO | 2014016692 A3 | 1/2014 |
| WO | 2014016693 A2 | 1/2014 |
| WO | 2014016693 A3 | 1/2014 |
| WO | 2014016694 A2 | 1/2014 |
| WO | 2014016694 A3 | 1/2014 |
| WO | 2014016697 A2 | 1/2014 |
| WO | 2014016697 A3 | 1/2014 |
| WO | 2014016700 A2 | 1/2014 |
| WO | 2014016700 A3 | 1/2014 |
| WO | 2014016701 A2 | 1/2014 |
| WO | 2014016701 A3 | 1/2014 |
| WO | 2014047310 A1 | 3/2014 |
| WO | 2014049448 A2 | 4/2014 |
| WO | 2014049448 A3 | 4/2014 |
| WO | 2014057361 A2 | 4/2014 |
| WO | 2014057361 A3 | 4/2014 |
| WO | 2014096969 A2 | 6/2014 |
| WO | 2014096969 A3 | 6/2014 |
| WO | 2014096971 A2 | 6/2014 |
| WO | 2014096973 A2 | 6/2014 |
| WO | 2014096973 A3 | 6/2014 |
| WO | 2014207576 A2 | 12/2014 |
| WO | 2014207576 A3 | 12/2014 |
| WO | 2015004540 A2 | 1/2015 |
| WO | 2015004540 A3 | 1/2015 |
| WO | 2015077283 A1 | 5/2015 |
| WO | 2015139053 A1 | 9/2015 |
| WO | 2017087681 A1 | 5/2017 |
| WO | 2017112960 A1 | 6/2017 |
| WO | 2017173433 A1 | 10/2017 |
| WO | 2020223723 A1 | 11/2020 |
| WO | 2020223738 A1 | 11/2020 |
| WO | 2020223740 A1 | 11/2020 |
| WO | 2021076188 A1 | 4/2021 |
| WO | 2022155632 A1 | 7/2022 |

OTHER PUBLICATIONS

Fairbanks, David W., et al. "Neurostimulation for Obstructive Sleep Apnea: Investigations." ENT Journal 72.1 (1993) 52-57.

Goding, Jr., George S., et al. "Relief of Upper Airway Obstruction With Hypoglossal Nerve Stimulation in the Canine." Laryngoscope 108 Feb. 1998, 162-169.

Tran, W. H., et al. "Development of Asynchronous, Intralingual Electrical Stimulation to Treat Obstructive Sleep Apnea" Proceedings of the 25th Annual International Conference of the IEEE EMBS Cancun, Mexico, Sep. 17-21, 2003, 375-378.

Tran, W. H., et al. "First Subject Evaluated with Simulated BION Treatment in Posterior Genioglossus to Prevent Obstructive Sleep Apnea." Proceedings of the 26th Annual International Conference of the IEEE EMBS San Francisco, CA, USA, Sep. 1-5, 2004, 4287-4289.

Yoo, Paul B. "Effects of selective hypoglossal nerve stimulation on canine upper airway mechanics" J Appl Physiol 99: 937-943, 2005.

International Search Report and Written Opinion mailed Apr. 22, 2022; International Application No. PCT/US2022/070101; 15 pages.

International Search Report and Written Opinion mailed Aug. 14, 2020, International Application No. PCT/US2020/031279, 19 pages.

International Search Report and Written Opinion mailed Feb. 10, 2015, International Application No. PCT/US2014/066311, 8 pages.

International Search Report and Written Opinion mailed Oct. 9, 2020, International Application No. PCT/US2020/031383, 13 pages.

International Search Report and Written Opinion mailed Sep. 7, 2020, International Application No. PCT/US2020/031266, 8 pages.

International Search Report and Written Opinion mailed Sep. 8, 2020, International Application No. PCT/US2020/031389, 9 pages.

Bailey , "Activities of human genioglossus motor units", Respiratory Physiology & Neurobiology 179:14-22, 2011.

Björninen, Toni , et al., "The Effect of Fabrication Method on Passive UHF RFID Tag Performance", International Journal of Antennas and Propagation, https://doi.org/10.1155/2009/920947, 2009, 8 pages.

Cienfuegos , et al., "Mandible—Surgical approach", Intraocular—AO Surgery Reference, v1 .0 Dec. 1, 2008—(Accessed Apr. 18, 2016).

Cienfuegos , et al., "Mandible—Surgical approach", Submental—AO Surgery Reference, v1 .0 Dec. 1, 2008—(Accessed Apr. 18, 2016).

Katz, Eliot S., et al., "Genioglossus activity during sleep in normal control subjects and children with obstructive sleep apnea", Am J Respir Crit Care Med. Sep. 1, 2004;170(5):553-60 (Year: 2004).

Schwartz , et al., "Electrical Stimulation of the Lingual Musculature in Obstructive Sleep Apnea", Journal of Applied Physiology 81:643-652, 1996.

* cited by examiner

INTRA-ORAL APPLIANCES AND SYSTEMS

CROSS-REFERENCE TO RELATED APPLICATIONS

This application is a continuation of U.S. patent application Ser. No. 16/865,363 filed May 3, 2020, which claims priority to U.S. Patent Application No. 62/842,890 filed May 3, 2019, the contents of which are incorporated herein by reference in their entireties.

TECHNICAL FIELD

An intra-oral appliance for powering and/or communicating with a neurostimulator is provided.

BACKGROUND

Preterm obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc. Continuous positive airway pressure (CPAP) is a standard treatment for OSA. While CPAP is non-invasive and highly effective, it is not well tolerated by patients. Patient compliance for CPAP is often reported to be between 40% and 60%. Surgical treatment options for OSA, such as anterior tongue muscle repositioning, orthognathic bimaxillary advancement, uvula-palatal-pharyngoplasty, and tracheostomy are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibulary advancement), and/or they may be socially stigmatic (e.g., tracheostomy) and involve extensive morbidity.

SUMMARY

Devices to power and/or communicate with a neurostimulator are provided herein. In an aspect, an energy delivery system is provided to activate and communicate with an indwelling neurostimulator placed proximate to a distal arborization of the hypoglossal nerve, within the genioglossus muscle, for example. An energy delivery system can include a removable intra-oral appliance that includes a remote controller for a neurostimulator. The energy coupling provides sufficient power to enable the neurostimulation device, using telemetric protocols, to modulate the delivery of a neurostimulation signal to a target site, such as, for example, the hypoglossal nerve. An intra-oral appliance can include a teeth covering configured to fit over mandibular incisor, canine and/or premolar teeth of a human being. The intra-oral appliance can also include a remote controller that is a hermetically sealed housing extending posteriorly from and operably connected to the teeth covering. The housing can comprise a power source, a coupling coil configured to transmit power to a neurostimulator and configured to receive power from an external charger, and a control circuit operably connected to the coupling coil and the power source. Neurostimulation systems are also provided that include an intra-oral appliance and a neurostimulator along with other components such as an external charger, a personal electronic device, and/or a programming device. Intra-oral appliances and systems including same can be used to improve sleep disordered breathing, including OSA, in patients suffering therefrom.

DETAILED DESCRIPTION

Devices for powering and/or communicating with neurostimulators are provided herein. The present disclosure refers to the term "substantially" with respect to certain shapes and configurations. By "substantially" is meant that the shape or configuration of the element need not have the mathematically exact described shape or configuration but can have a shape or configuration that is recognizable by one skilled in the art as generally or approximately having the described shape or configuration. The terms "anterior" and "posterior" are used herein with reference to a patient in a standard anatomical position. Further, as used herein with respect to a described element, the terms "a," "an," and "the" include at least one or more of the described element, including combinations thereof, unless otherwise indicated. Further, the term "or" refers to "and/or" and "combinations thereof" unless otherwise indicated. By "integral" or "integrated" is meant that the described components are fabricated as one piece or multiple pieces affixed during manufacturing or the described components are otherwise not separable using a normal amount of force without damaging the integrity (i.e. tearing) of either of the components. A normal amount of force is the amount of force a user would use to remove a component meant to be separated from another component without damaging either component. As used herein a "patient" includes a mammal such as a human being.

Figure 1:
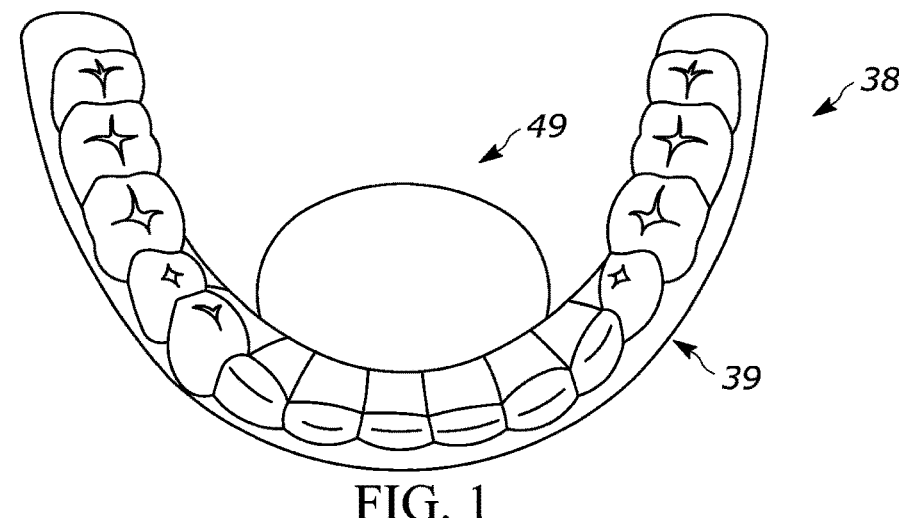
FIG. 1 is top view of an intra-oral appliance according to an aspect of the present disclosure.
Figure 2:
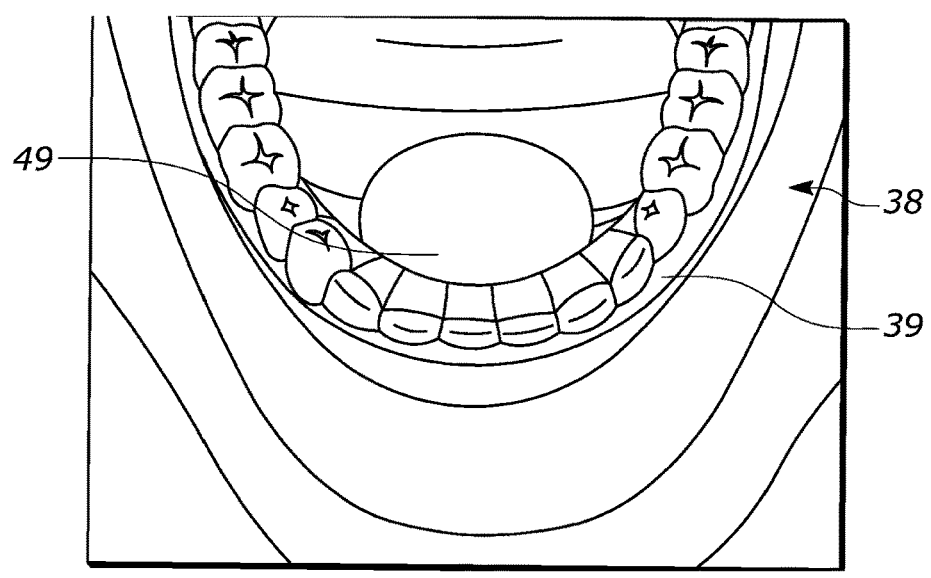
FIG. 2 is a top view of an intra-oral appliance positioned on a patient's teeth according to an aspect of the present disclosure.
Figure 3:
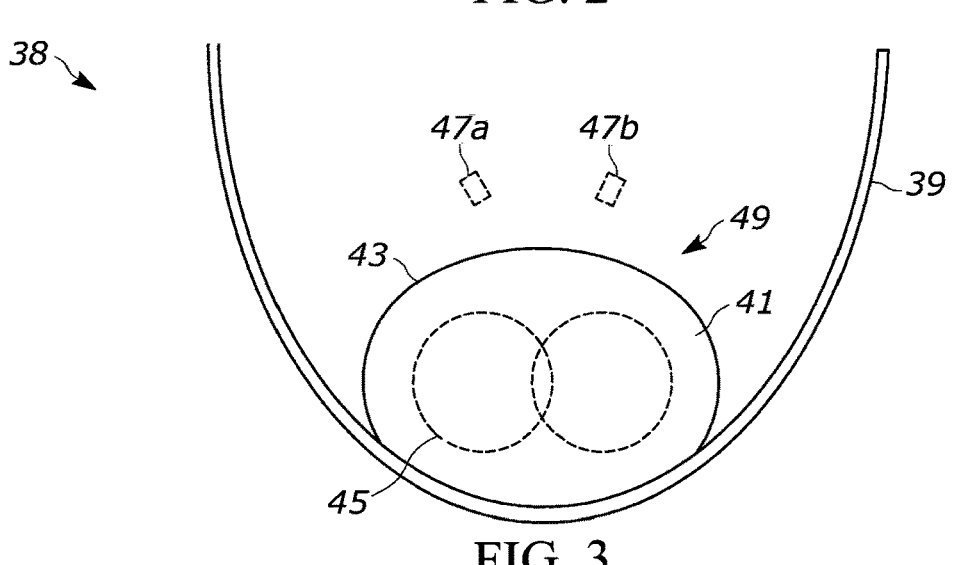
FIG. 3 is a top schematic view of an intra-oral appliance in spatial relation to implanted neurostimulators according to an aspect of the present disclosure.

An intra-oral appliance that includes a remote controller for powering and/or communicating with a neurostimulator is provided herein. Referring to FIGS. 1 to 3, intra-oral appliance 38 is configured to sit on the lower jaw or mandible of a patient suffering from sleep disordered breathing and temporarily affixes to the posterior surface of the teeth and rests underneath the tongue. In particular, intra-oral appliance 38 can comprise a mouthguard or teeth covering 39 having a substantially semi-circular shape configured to fit over a patient's mandibular incisor, canine and/or premolar teeth. Intra-oral appliance 38 can further include a remote controller 49 in the form of a housing 41 extending posteriorly from and operably connected to teeth covering 39 and configured to be positioned underneath the ventral surface of the tongue in an operable configuration (i.e. when therapy is ready to be initiated and the intra-oral appliance is worn by the patient). The teeth covering and housing can be an integral one-piece device. The housing can have a substantially ellipsoidal shape and can have a thickness of less than or equal to approximately five millimeters (mm) and an ellipsoidal diameter of less than or equal to three centimeters (cm). The geometry of intra-oral appliance naturally encourages the lower jaw to be positioned more anterior than normal thereby assisting with the opening of the patient's airway.

FIG. 2 is a schematic illustration of a top view of intra-oral appliance 38 depicting internal components of intra-oral appliance 38. Remote controller 49 can house a rechargeable or removable power source 43 and one or more coupling coils 45 arranged in a power/communication circuit such that power source 43 can provide electrical power for exciting coupling coils 45. Exciting coils 45 create a magnetic field that can reach one or more implanted neurostimulators 47. Neurostimulators 47 can include a coil and/or an antenna that is excited by the electromagnetic field generated by coupling coils 45, which induces a current in the neurostimulator coil/antenna. Through inductive coupling, the induced current can be used to power the implanted neurostimulators 47 for an extended period of time. For example, a rechargeable battery can provide as much as eight hours of power to a neurostimulator through this inductive coupling configuration.

It should be noted that neurostimulators 47 are individual components that are separate from the intra-oral appliance 38. FIG. 2 illustrates the relative spatial relationship between neurostimulators 47 and intra-oral appliance 38. The neurostimulators are implanted at a target site of neural or neuromuscular tissue, as described in more detail below. In the illustrated example configuration of the system, the intra-oral appliance 38 has no stimulating or sensing electrodes, as its purpose is to wirelessly power the implanted neurostimulators 47 through inductive coupling. However, the intra-oral appliance could have stimulating and/or sensing electrodes to stimulate tissue with the oral cavity and sense parameters within the oral cavity, such as tongue position, for example.

Figure 4:
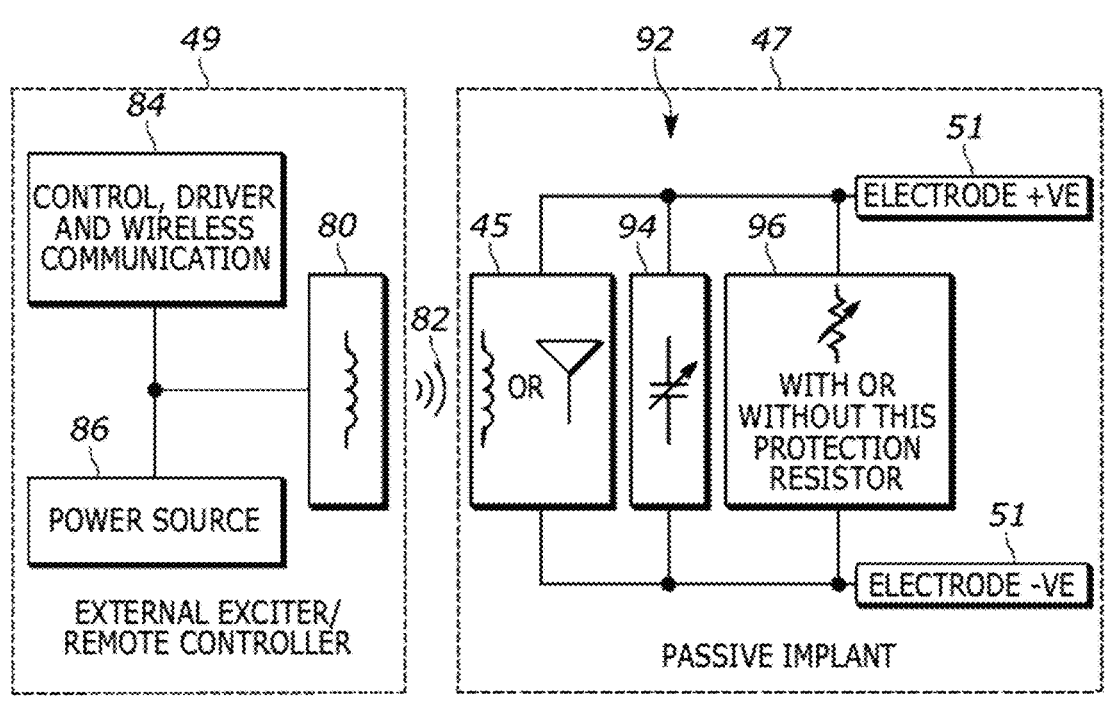
FIG. 4 is a block diagram illustrating components of a neurostimulator and a remote controller of an intra-oral appliance according to an aspect of the present disclosure.

Referring to FIG. 4, according to one aspect, neurostimulators 47 can be passive devices. By this, it is meant that the stimulation parameters with which neurostimulators 47 deliver electrical stimulation are determined by the current induced in the neurostimulators by remote controller 49. These stimulation parameters can, for example, include the amplitude, frequency, wavelength, waveform, pulse width, pulse phase, and polarity of the electrical stimulation signal. Remote controller 49 can include a control circuit 84, which includes, among other components, a microprocessor and memory used to store executable code, programming data, stimulation parameters, and other data, which the microprocessor uses to execute the control functions described herein. Control circuit 84 can be configured to utilize power source 86 to supply current to coupling coil 80 that displays signal characteristics defined by the desired stimulation parameters. The stimulation parameters can be programmed onto control circuit 84 via wireless communication, e.g., Bluetooth or wifi radio communication. This programming can be done through any Bluetooth enabled device, such as a smartphone, tablet computer, notebook computer, PC, etc. Other parameters, such as patient information, history, data logging, etc., can also be communicated in this manner.

Control circuit 84 can supply the current to the coupling coil with the desired signal characteristics, for example, through pulse-width modulation ("PWM"). Coupling coil 80, excited by this current, creates an electromagnetic field 82 that displays these same signal characteristics. Coils/antenna 45 of the neurostimulator are, in turn, excited by this field 82, which causes the current induced therein to have the same or substantially the same signal characteristics. Coils/antenna 45 form portions of a neurostimulator circuit 92 that includes a charge storage device 94, stimulation electrodes 51, and, optionally, a protection resistor/circuit 96. This induced current flows charges charge storage device 94 (e.g., a capacitor), which supplies electrodes 51. Electrodes 51 deliver the electrical stimulation with the signal characteristics of the induced current. It can thus be seen that, in this passive implementation of neurostimulator 47, the signal is passed through the device as received from remote controller 49.

In use, remote controller 49 can control neurostimulators 47 in an open loop control scheme, as described above. Alternatively, the neurostimulators can include sensors that provide feedback that can be relayed back to control circuit 84 for closed-loop control. Other devices, such as an external, wearable sensor or implantable sensor can be used to provide feedback. In one specific example, the sensors can be electrodes 51 or sensors implemented in neurostimulators 47. Remote controller 49 can apply stimulation via neurostimulators 47 according to stimulation program(s) stored in control circuit 84 memory. Stimulation programs can include predetermined, set programs (e.g., firmware) and adaptive, dynamic programs (e.g., software that is configurable/adaptable). The remote controller can select between various programs and/or actively modify a stimulation program according to various inputs received via Bluetooth from a smartphone, tablet, etc. from a patient or doctor.

Figure 5:
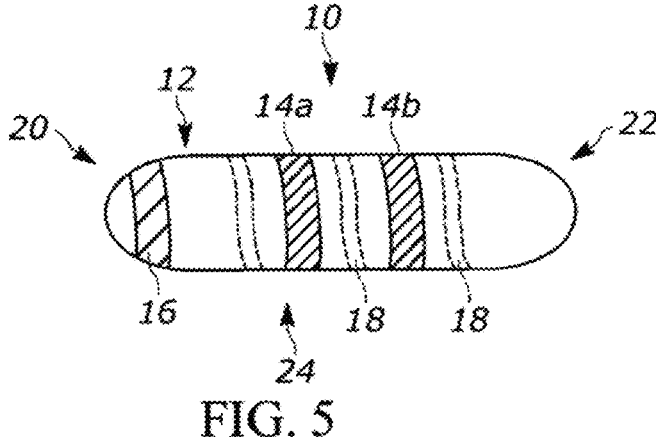
FIG. 5 is a side view of a neurostimulator according to an aspect of the present disclosure.

The neurostimulator that is powered and communicates with an intra-oral appliance as described herein can be an implantable neurostimulator such as an indwelling neurostimulator as described in U.S. Provisional Application No. 62/659,347 ("the '347 application). The '347 application describes an injectable implant. Referring to FIG. 5, injectable implant 10 can comprise a body 12, a stimulating electrode 14 disposed on the body, and an antenna or coil 16 that is connected to the body for receiving power and/or stimulation parameters from a remote controller. Injectable implant 10 can also include a deployable fixation structure 18 that is housed within the body in a non-deployed configuration and, when actuated, forms a surface structure on the body that facilitates fixation in or about a target tissue. Body 12 can comprise a hermetically-sealed structure that has a generally tubular or cylindrical shape (e.g., isodiametric). In some instances, body 12 can have a hermetic integrity such that the leak rate is less than about $5\times10^{-8}$ atm cc/s He, and that moisture within the body through its service life is less than about 6000 ppm. Body 12 can include a proximal end portion 20, a distal end portion 22, and a middle portion 24 extending between the proximal and distal end portions. In one example, body 12 can have an outer diameter that is less than or equal to 5 mm and, for example, less than or equal to 2 mm. In another example, body 12 can have a length of about 50 mm or less, e.g., about 40 mm (e.g., about 30 mm), about 10 mm or 5 mm.

Figure 6:
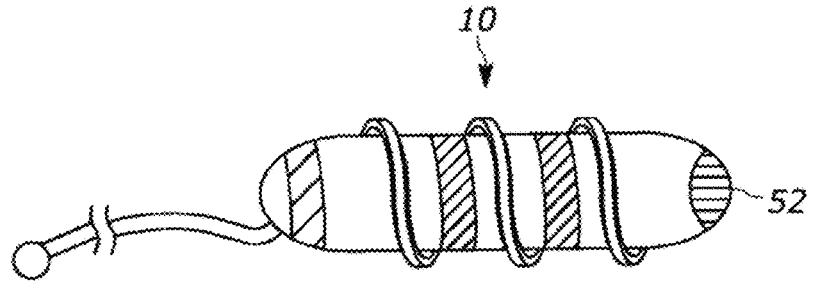
FIG. 6 is a side view of a neurostimulator according to an aspect of the present disclosure.

As also shown in FIG. 6, implant 10 can include a sensor 52 to enable closed-loop operation of the implant. Sensor 52 can be disposed on body 12 and be configured or programmed to detect at least one physiological parameter, or a related symptom, associated with sleep disordered breathing, such as OSA. In one example, implant 10 can include an electromyography EMG) sensor 52 that is capable of detecting the electrical activity produced by a muscle. Examples of muscles whose activity can be detected by an EMG sensor of the present disclosure are disclosed in U.S. Pat. No. 9,757,560 to Papay, which is incorporated by reference herein. In certain aspects, implant 10 can include an electrode capable of stimulation and sensing; in other words, a dual capacity electrode. The above-described neurostimulator is only exemplary and an intra-oral appliance can be used with other neurostimulators. In certain embodiments, the indwelling neurostimulator is positioned at a distal arborization 90 of the hypoglossal nerve 92 as illustrated in FIG. 7 (implant 10 enlarged for purposes of illustration).

Figures 7, 8:
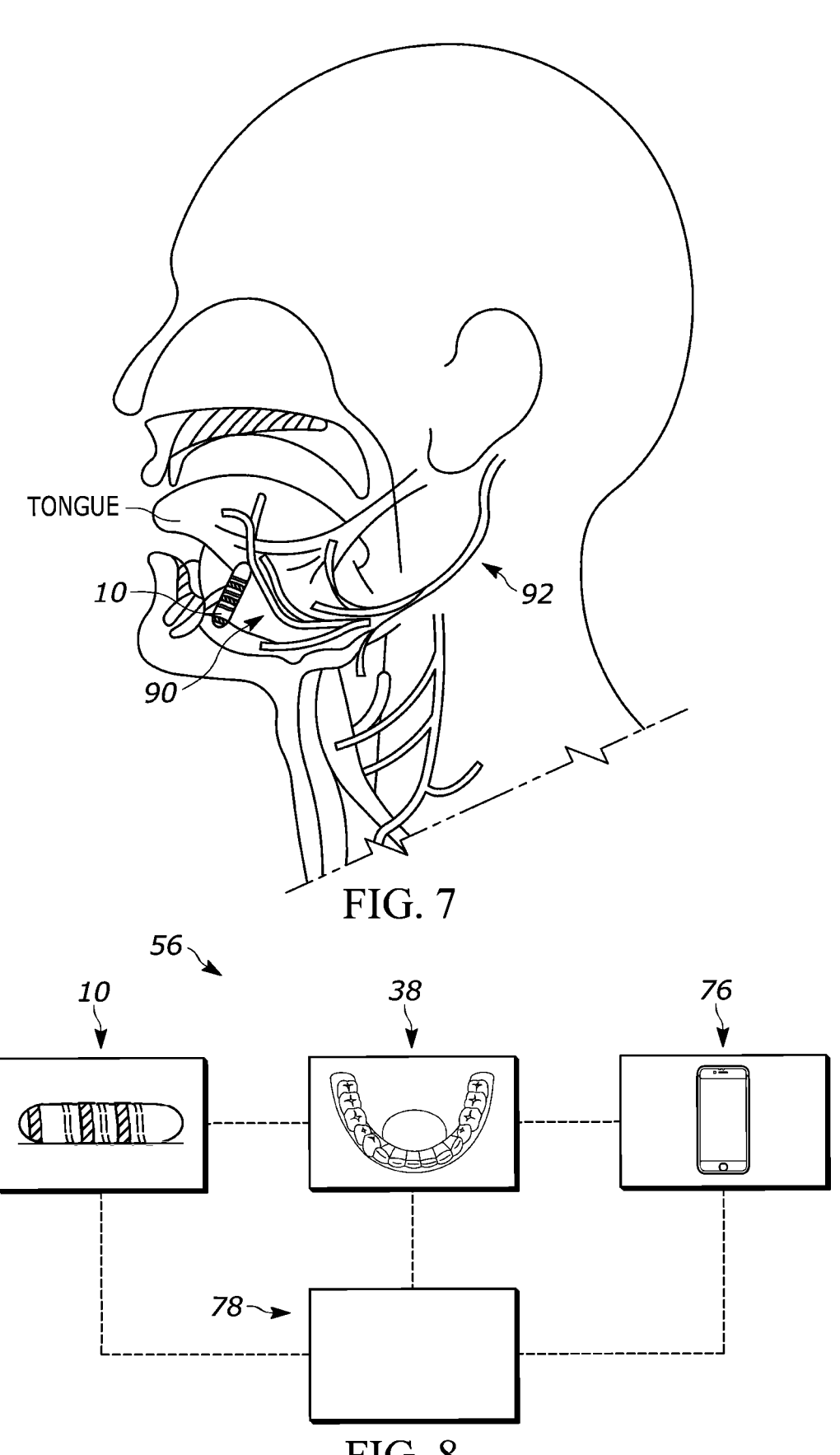
FIG. 7 is a schematic illustration of a neurostimulator implanted in a target site of a patient's body according to an aspect of the present disclosure.
FIG. 8 is a block diagram of components of a neurostimulation system according to an aspect of the present disclosure.

Additional components of a neurostimulator system 56 are illustrated in FIG. 8 and can include intra-oral appliance 38, a personal electronic device 76, and a programming device 78. As shown in FIG. 8, neurostimulator 10 (which in FIG. 8 is illustrated as an injectable neurostimulator as described above but could have forms and configurations) can be in electrical communication (e.g., wireless communication) with intra-oral appliance 38 and programming device 78 (which is illustrated as a smartphone but could take other forms); the intra-oral appliance can be in electrical communication (e.g., wireless communication) with neurostimulator 10, the personal electronic device 76, and the programming device 78; the personal electronic device 76 can be in electrical communication (e.g., wireless communication) with the intra-oral appliance 38 and the programming device 76; and the programming device 78 can be in electrical communication (e.g., wireless communication) with the personal electronic device 76, the intra-oral appliance 38, and the neurostimulator 10.

All or only certain components of system 56 can be portable and adapted to be borne by a patient suffering from sleep disordered breathing for a desired period of time. In some instances, system 56 can be borne by a subject for an acute period of time (e.g., during an emergency situation), for a semi-chronic period of time (e.g., less than about a week to about 6 weeks), or for a chronic period of time (e.g., greater than about 6 weeks). For example, the neurostimulator can be temporarily or permanently implanted within, on, or otherwise associated with a subject suffering from sleep disordered breathing. The intra-oral appliance can be electrically coupled to an indwelling neurostimulator to deliver power and control signals to activate the neurostimulator, for example, during an eight hour treatment period, for sleep disordered breathing such as OSA.

Programming device 78 of system 56 can be configured and programmed to deliver stimulation and/or control instructions to the intra-oral appliance 38, and/or neurostimulator 10, and/or personal electronic device 76. In one example, programming device 78 can be configured as a dedicated, smart phone-sized unit. In another example, programming device 78 can be configured as a smart phone accessory dongle. In some instances, programming device 78 can be operated manually by the patient or a caregiver. In other instances, the programming device 78 can be battery powered and/or directly powered, e.g., by an AC source. If powered by rechargeable batteries, a battery charger may be an accessory to the programming device 78.

With respect to personal electronic device 76 of system 56, examples of personal electronic devices include smart phones and tablets; although, it will be appreciated that personal computers (PCs) may also be included. In some instances, the personal electronic device can include software programmed to control one or more stimulation and/or control parameters associated with the neurostimulator. Additionally, or optionally, the software comprising the personal electronic device can be programmed to store patient therapy data, such as diary questions and patient incentive information, and/or promote patient-to-patient interaction. The personal electronic device can also include software programmed to access remote data sources (e.g., Internet websites), query certain data, and then provide stimulation instructions to the system 56 based on the queried data. In another example, the personal electronic device can also include software programmed to provide the neurostimulator with customizable or patient-triggered alerts, e.g., indicating stimulation periods and the duration of each period, after a desired period of time after sleep onset, or after consumption of food or water. In some instances, the personal electronic device can be operated manually by the patient or a caregiver.

System 56 can be configured as an open-loop or closed-loop system. In an open-loop system, for example, a physician or the subject may, at any time, manually or by the use of pumps, motorized elements, etc., adjust treatment parameters of the system 56. Alternatively, in a closed-loop system (discussed below), treatment parameters (e.g., electrical signals) may be automatically adjusted in response to a sensed physiological parameter or a related symptom indicative of the extent of sleep disordered breathing, such as OSA. In a closed-loop feedback system, a sensor that senses a physiological parameter associated with sleep disordered breathing, such as OSA (e.g., muscle or nerve electrical activity, tongue position, oropharyngeal airflow, etc.) can be utilized. More detailed descriptions of sensors that may be employed in a closed-loop system, as well as other examples of sensors and feedback control techniques that may be employed as part of the present disclosure are disclosed in U.S. Pat. No. 5,716,377, which is incorporated by reference herein.

Figure 9:
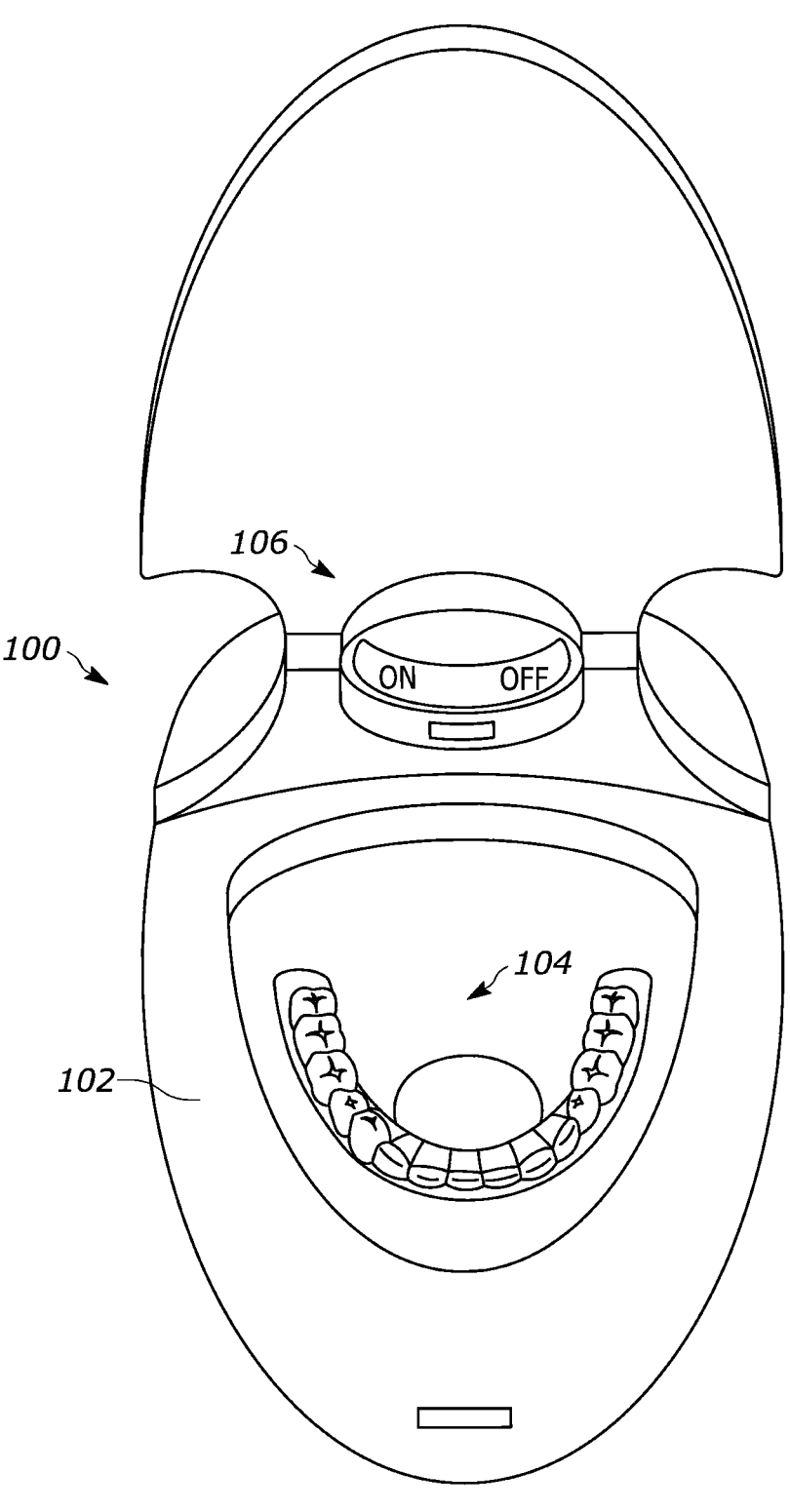
FIG. 9 is a perspective view of a re-charging device according to an aspect of the present disclosure.

Referring to FIG. 9, a neurostimulator system can include external recharging device 100 that incorporates wireless charging functionality by way of a wireless charging/coupling pad or coil incorporated into housing 102 of external recharging cradle 100 to re-charge an intra-oral appliance 104. Current from an internal or external power source can flow through the coil/pad inside recharging device 100, creating an electromagnetic field. Such an electromagnetic field can induce current in a coupling coil (e.g. inductive coupling) of intra-oral appliance 104 that is in electrical communication with the intra-oral appliance's battery. Such current can recharge the battery of the intra-oral appliance. As such, the external recharging device can provide wireless recharging of the remote controller of the intra-oral appliance. The external recharging device can also provide gentle ultrasonic or chemical cleaning of the teeth covering of the intra-oral appliance. The cleaning can be similar to other ultrasonic or chemical based cleaning system. The external recharging device can include a display 106 that indicates that the charging and cleaning function is either "off," "in progress" or "complete" by way of a multi-color indicator, for example. The wireless recharging function can provide a complete charge in 120 minutes using a 5V, 2 A power source, for example.

Each of the disclosed aspects and embodiments of the present disclosure may be considered individually or in combination with other aspects and embodiments. Further, while certain features of embodiments may be shown in only certain figures, such features can be incorporated into other embodiments shown in other figures or otherwise disclosed in the specification. Additionally, when describing a range, all points within that range are included in this disclosure. In addition, unless otherwise specified, none of the steps of the methods of the present invention are confined to any particular order of performance.

We claim:

1. A neuromodulation system comprising:
an injectable neurostimulator configured to be injected into a head of a patient and configured to deliver stimulation energy to at least one of a muscle or a nerve of the patient, the neurostimulator comprising a body, an electrode carried by the body, and an antenna carried by the body and electrically coupled to the electrode, wherein the body of the neurostimulator comprises:
a first end portion having a domed shape,
a second end portion,
a longitudinal axis extending between the first and second end portions, and
an intermediate portion extending between the first and second end portions, and
a helical fixation structure having a portion extending away from the second end portion, and
wherein the electrode is disposed along the intermediate portion of the body; and
an intra-oral appliance comprising:
a teeth covering configured to be positioned on one or more of the patient's teeth; and
a coil configured to create a magnetic field for inductively coupling to the antenna of the neurostimulator to deliver power to the neurostimulator.

2. The system of claim 1, wherein the coil is a first coil and the system further comprising an external power source comprising a second coil configured to create a magnetic field for inductively coupling to the first coil of the intra-oral appliance to deliver power to the intra-oral appliance.

3. The system of claim 2, wherein the intra-oral appliance comprises at least two coils.

4. The system of claim 3, wherein at least one of the at least two coils is configured to inductively couple to the antenna of the neurostimulator and at least one of the at least two coils is configured to inductively couple to the second coil of the external power source.

5. The system of claim 1, wherein the second end portion has a domed shape.

6. The system of claim 1, wherein the electrode extends circumferentially around the body.

7. The system of claim 1, wherein the neurostimulator is configured to be positioned proximate a distal arborization of a hypoglossal nerve of the patient.

8. The system of claim 1, wherein the neurostimulator is configured to be positioned within a genioglossus muscle of the patient.

9. The system of claim 1, wherein the neurostimulator is a first neurostimulator, the system further comprising a second neurostimulator.

10. The system of claim 9, wherein the second neurostimulator is configured to be positioned at a contralateral side of the patient's head relative to a side of the patient's head at which the first neurostimulator is positioned.

11. The system of claim 9, wherein the first neurostimulator is configured to deliver stimulation energy to a right hypoglossal nerve or a left hypoglossal nerve and the second neurostimulator is configured to deliver stimulation energy to the other of the right hypoglossal nerve or the left hypoglossal nerve.

12. The system of claim 1, wherein the system comprises a control circuit configured to operate the neurostimulator in a closed-loop control scheme.

13. The system of claim 1, wherein the neurostimulator comprises a sensor configured to detect a physiological parameter or a related symptom associated with sleep disordered breathing.

14. The system of claim 13, wherein the sensor is an electromyography (EMG) sensor.

15. The system of claim 1, further comprising an external sensor configured to provide feedback for operating the neurostimulator in a closed-loop control scheme.

16. The system of claim 1, wherein the helical fixation structure is configured to secure the neurostimulator to tissue in the head of the patient.

17. The system of claim 1, wherein the neurostimulator has a length of about 50 millimeters or less.

18. The system of claim 1, wherein the neurostimulator is hermetically sealed.

19. The system of claim 1, wherein the teeth covering is configured to be positioned on teeth of a lower jaw of the patient.

20. The system of claim 1, wherein the domed shape is hemispherical.

21. The system of claim 1, wherein the domed shape is curved along a circumferential dimension and a longitudinal dimension.

* * * * *